(12) United States Patent
Biausque et al.

(10) Patent No.: US 11,498,888 B2
(45) Date of Patent: Nov. 15, 2022

(54) CATALYSTS AND METHODS FOR DIMERIZING PROPYLENE

(71) Applicant: SABIC Global Technologies B.V., Bergen op Zoom (NL)

(72) Inventors: Gregory Biausque, Thuwal (SA); Dirk Beetstra, Thuwal (SA); Abdulaziz Abdullah Ahmed, Thuwal (SA); Faisal Fahd Alahmadi, Thuwal (SA); Justin R. Johnson, Thuwal (SA); Edrisse Chermak, Thuwal (SA); Raeid Sadeq, Thuwal (SA); Sari O. Alsayegh, Thuwal (SA); Aspi Kersasp Kolah, Thuwal (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 17/250,360

(22) PCT Filed: Jul. 11, 2019

(86) PCT No.: PCT/IB2019/055898
§ 371 (c)(1),
(2) Date: Jan. 11, 2021

(87) PCT Pub. No.: WO2020/012393
PCT Pub. Date: Jan. 16, 2020

(65) Prior Publication Data
US 2021/0253494 A1 Aug. 19, 2021

Related U.S. Application Data

(60) Provisional application No. 62/696,504, filed on Jul. 11, 2018.

(51) Int. Cl.
*C07C 2/10* (2006.01)
*B01J 21/06* (2006.01)
(Continued)

(52) U.S. Cl.
CPC .............. *C07C 2/10* (2013.01); *B01J 21/066* (2013.01); *B01J 23/02* (2013.01); *B01J 23/10* (2013.01);
(Continued)

(58) Field of Classification Search
CPC ......... C07C 2/10; C07C 2/24; C07C 2521/06; C07C 2523/04; B01J 21/066; B01J 23/02; B01J 23/10; B01J 37/08
See application file for complete search history.

(56) References Cited

U.S. PATENT DOCUMENTS 4,774,215 A * 9/1988 Drake .................... B01J 27/232
502/174
4,939,313 A * 7/1990 Drake .................... B01J 27/232
585/516
(Continued)

FOREIGN PATENT DOCUMENTS

EP 0993865 4/2000

OTHER PUBLICATIONS

International Preliminary Reporton Patentability issued in corresponding International application No. PCT/IB2019/055898 dated Sep. 22, 2020.
(Continued)

*Primary Examiner* — Ali Z Fadhel
(74) *Attorney, Agent, or Firm* — Norton Rose Fulbright US LLP

(57) ABSTRACT

Catalysts for producing a branched aliphatic alkene are described. The catalyst can include a catalytic alkali metal or alkali metal composite on a mixed metal oxide support that includes a Column 1 metal and at least one of a Column 3 metal, a Column 4 metal or a lanthanide. The catalyst can have less than 50 wt. % of a metal carbonate. Methods of producing branched aliphatic alkenes by contacting the catalyst of the present invention with an aliphatic alpha olefin are also described.

19 Claims, 4 Drawing Sheets

(51) Int. Cl.
  *B01J 23/02* (2006.01)
  *B01J 23/10* (2006.01)
  *C07C 2/24* (2006.01)

(52) U.S. Cl.
  CPC ............ *C07C 2/24* (2013.01); *C07C 2521/06* (2013.01); *C07C 2523/04* (2013.01)

(56) References Cited

U.S. PATENT DOCUMENTS

| | | | |
|---|---|---|---|
| 5,105,049 A * | 4/1992 | Hasselbring | B01J 27/232 |
| | | | 585/516 |
| 5,334,794 A | 8/1994 | Fushimi et al. | |
| 6,262,325 B1 | 7/2001 | Narbeshuber et al. | |

OTHER PUBLICATIONS

International Search Report and Written Opinion issued in corresponding International application No. PCT/IB2019/055898 dated Dec. 18, 2019.

O'Connor et al., "Alkene oligomerization", *Catalysis Today*, 6(3):329-349, 1990.

Peltzer et al., "Characterization of potassium doped $Li_2ZrO_3$ based $CO_2$ sorbents: Stability properties and $CO_2$ desorption kinetics", *Chemical Engineering Journal*, 336:1-11, 2018.

Xiao et al., "Citrate route to prepare K-doped $Li_2ZrO_3$ sorbents with excellent $CO_2$ capture properties", *Chemical Engineering Journal*, 174:231-235, 2011.

* cited by examiner

US 11,498,888 B2

CATALYSTS AND METHODS FOR DIMERIZING PROPYLENE

CROSS REFERENCE TO RELATED APPLICATIONS

This application is a national phase application under 35 U.S.C. § 371 of International Application No. PCT/IB2019/055898 filed Jul. 11, 2019, which claims the benefit of priority of U.S. Provisional Application No. 62/696,504 filed Jul. 11, 2018, all of which are hereby incorporated by reference in their entirety.

BACKGROUND OF THE INVENTION

A. Field of the Invention

The invention generally concerns methods of producing branched aliphatic alkenes via dimerization reactions. In particular, the invention concerns reacting a feed stream that includes aliphatic alpha olefins with a supported alkali metal or alkali metal composite catalyst to produce a branched aliphatic alkene. The catalyst support can include a mixed metal oxide that includes a Column 1 metal and at least one Column 3 metal, Column 4 metal, a lanthanide metal, or any combination thereof.

B. Description of Related Art

Catalysts for the dimerization of α-olefins are known. For instance, the industrially viable routes to products produced from the dimerization of propylene (e.g., 4-methyl-1-pentene) with high selectivity include potassium metal and potassium carbonate, or using specifically designed metallocene catalysts. One such example includes U.S. Pat. No. 4,774,215 to Drake et al. This patent describes a catalyst that includes an alkali metal and divided glass on an alkali metal carbonate support with an optional metal oxide in a 1:1 to 1:10 metal oxide to alkali metal carbonate. In another example, U.S. Pat. No. 6,262,325 to Narbeshuber et al. describes a catalyst for side-chain alkylation or alkenylation of alkylaromatic or alkylalicyclic compounds with olefins or diolefins. In particular, this patent uses a catalyst having an alkali metal on a support that includes divalent metals positioned on a Ti, Zr, Hf, or TiZr oxide material. The catalyst had a selectivity for methyl pentene of less than 40%. In yet another example, U.S. Pat. No. 5,105,049 to Hasselbring describes a dimerization catalyst that includes an alkali metal on an alkali metal carbonate support.

While alkali metal on carbonate catalysts have high selectivity for methyl propene or side chain reactions for aromatic compounds, they suffer in that they have a rather long induction time (e.g., 10 hours or more) and can structurally degrade during use. Moreover, the use of metallic potassium can strongly limit the nature of the supporting material. Potassium metal is strongly reducing and reactive towards many typical supports (e.g., turning alumina into potassium aluminates, and silica into potassium silicates).

SUMMARY OF THE INVENTION

A discovery has been made that addresses at least some of the problems associated with catalysts used for dimerization of olefins to produce hydrocarbons having a higher carbon number (e.g., dimerization of aliphatic alpha olefins to produce branched aliphatic alkenes). The solution is premised on the use of an alkali metal supported on a mixed metal oxide support to convert aliphatic alpha olefins to branched aliphatic alkenes. The mixed metal oxide includes a Column 1 metal and at least one of a Column 3 metal, a Column 4 metal, or a lanthanide metal. The support includes less than 50 wt. % of a metal carbonate (e.g., less than 0 to 49 wt. % of $K_2CO_3$).

In one aspect of the invention, methods of producing a branched aliphatic alkene are described. A method can include reacting a feed stream that includes aliphatic alpha olefins (e.g., olefins having a carbon number of 1 to 5, 2 to 4, or about 3) with a supported alkali metal or alkali metal composite catalyst to produce the branched aliphatic alkene (e.g., a branched aliphatic alkene that has a carbon number from 4 to 10, preferably 4 to 8, more preferably 6, more preferably 4-methyl-1-propene). The feed stream can include propylene, optionally ethylene, a saturated hydrocarbon, or a mixture thereof. The support material can include a mixed metal oxide that includes a Column 1 metal (e.g., sodium (Na), potassium (K), and cesium (Cs), preferably K) and at least one Column 3 metal (e.g., scandium (Sc) or yttrium (Y), preferably Y), a Column 4 metal (e.g., titanium (Ti), zirconium (Zr), hafnium (Hf), preferably Zr), or a lanthanide oxide (e.g., lanthanum (La), cerium (Ce), promethium (Pm), or praseodymium (Pr), preferably La) or composites thereof. The support can include less than 50 wt. % of a metal carbonate. The alkali metal can be Na, K, Cs, or a composite, or a mixture thereof. In one instance, the alkali metal is K. In another instance, the alkali metal is a NaK composite or amalgam. The catalyst can include 0.1 to 10 wt. % of the alkali metal, preferably 1 to 9 wt. %, more preferably 3 to 8 wt. %, and all ranges and values there between. In some instances, the catalyst can be a K metal supported on sodium yttriate, potassium zirconate, or a mixture thereof. In another instance the catalyst can be a NaK metal composite supported on sodium yttriate, potassium zirconate, or a mixture thereof. The support material can be macroporous (pores having a diameter of greater than 50 nanometers (nm)), mesoporous (pores having a diameter of 2 nm 50 nm), or microporous (pores having a diameter of less than 2 nm) or a combination thereof. In some instances, the catalyst has an average particle diameter of 100 to 600 microns, an average pore volume of 0.03 to 0.30 mL/g, or both. Reaction conditions can include temperature, pressure, at liquid hourly space velocity (LHSV), or combinations thereof. Reaction temperatures can range from 120° C. to 200° C. more preferably 140° C. to 170° C. Reaction pressure can range from 5 MPa to 10 MPa. LHSV can range between 0.1 $h^{-1}$ to 2 $h^{-1}$. In some embodiments, the dimerization reaction is carried out in a reaction system comprising a pressurized reactor. Preferably, the pressurized reactor is a fixed bed reactor equipped with a cooling jacket. In some aspects, the reaction system can comprise two or more, preferably 2 to 5, of the reactors operated in parallel. The catalyst in the two or more reactors can have different activity levels. In some instances, at least one of the two or more reactors can be in regeneration mode, in which the reactor is not on-stream for producing the branched aliphatic alkene(s) while the catalyst is being regenerated. In some embodiments, the reaction system can comprise a first reactor and a second reactor operated in series; and a separation column disposed downstream to the first reactor and upstream to the second reactor. The separation column can be configured to remove the branched aliphatic alkene and isomers thereof from an effluent of the first reactor to produce an inlet stream for the second reactor. In a particular instance, the catalyst is a potassium metal or a NaK composite on sodium zirconate and the branched aliphatic alkene selectivity can be at least 92% after 6 hours. In some embodiments, the catalyst can be a NaK composite on potassium zirconate and the branched aliphatic alkene selectivity can be at least 97%.

In yet another instance, catalysts for producing a branched aliphatic alkene are described. A catalyst can include a potassium (K) metal or a NaK metal composite on a metal oxide support that can include a mixed metal oxide of a Column 1 metal and at least a Column 3 metal, a Column 4 metal, a lanthanide metal or a composite thereof, wherein the catalyst has less than 50 wt. % carbonate.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions and kits of the invention can be used to achieve methods of the invention.

The following includes definitions of various terms and phrases used throughout this specification.

An aliphatic compound is an acyclic or cyclic, saturated or unsaturated carbon group, excluding aromatic compounds. A linear aliphatic group does not include tertiary or quaternary carbons. A branched aliphatic group includes at least one tertiary and/or quaternary carbon. A cyclic aliphatic group is includes at least one ring in its structure. Polycyclic aliphatic groups may include fused, e.g., decalin, and/or spiro, e.g., spiro[5.5]undecane, polycyclic groups.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %", "vol. %", or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The methods and catalysts of the present invention can "comprise," "consist essentially of," or "consist of" particular ingredients, components, compositions, etc. disclosed throughout the specification. With respect to the transitional phrase "consisting essentially of," in one non-limiting aspect, a basic and novel characteristic of the catalysts and methods of the present invention are their abilities to catalyze dimerization of olefins (e.g., propylene to 4-methylpentene (4M1P).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 1A shows a schematic diagram of a system that includes a single reactor containing the catalyst for catalyzing dimerization of olefin(s); FIG. 1B shows a schematic diagram of a system that includes two parallel reactors containing the catalyst for catalyzing dimerization of olefin(s); and FIG. 1C shows a schematic diagram of a system that includes two reactors containing the catalyst for catalyzing dimerization of olefin(s) where the unreacted olefin(s) in an effluent from the first reactor is fed into the second reactor.

Figure 1A:
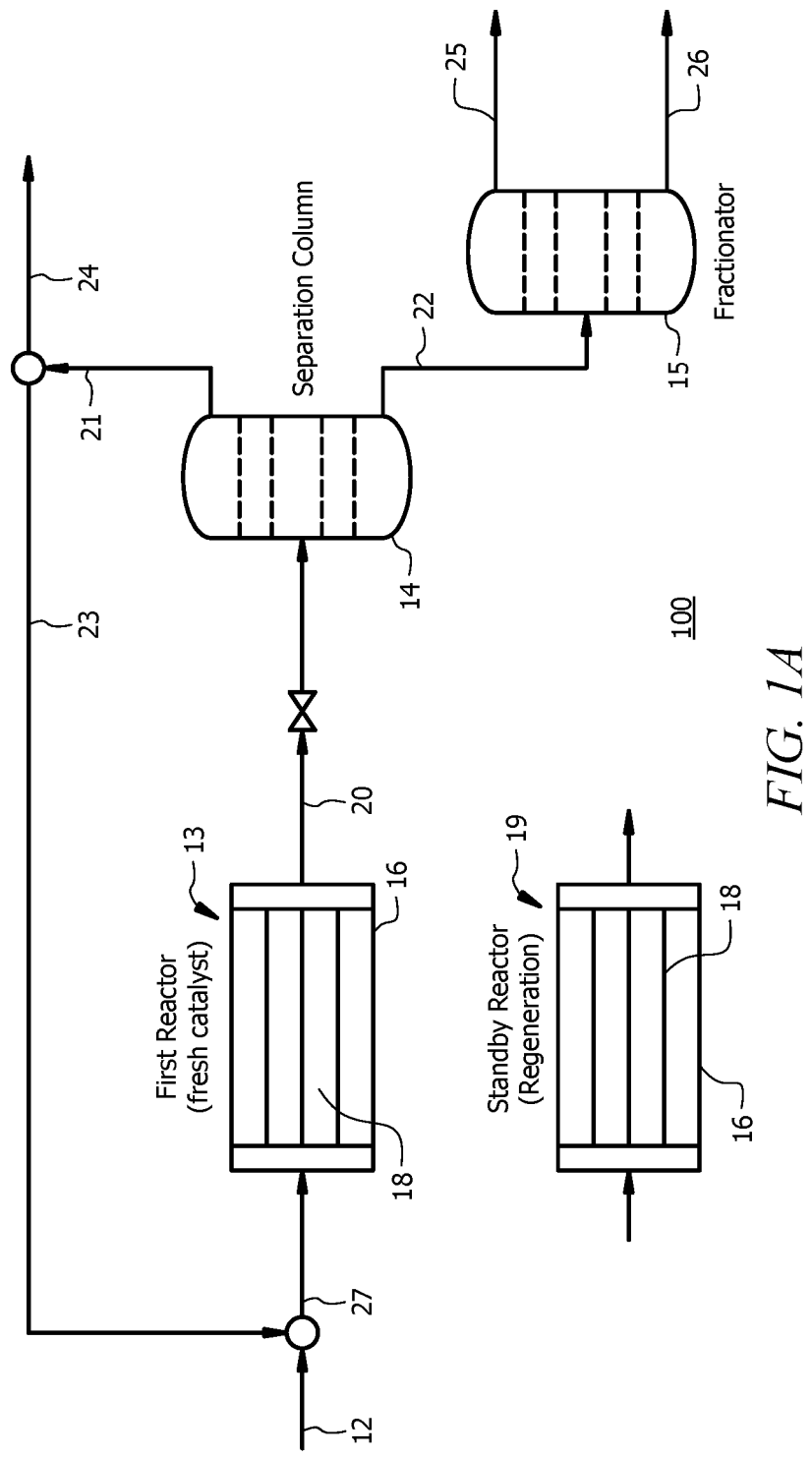
FIGS. 1A-1C show schematic diagrams of systems to perform the method of the present invention.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to at least some of the problems associated with using carbonates as support materials for dimerization reactions. The discovery is premised on the idea of reacting a feed stream that includes reactive olefins with a catalytic alkali metal on a mixed metal oxide support that includes less than 50 wt. % carbonate material. Use of such a catalyst provides a more efficient method of producing the catalyst, improved induction time (e.g., minutes rather than hours), and improved structural properties (e.g., the catalyst does not collapse or degrade over time). The support can include a Column 1 metal oxide and at least one of a Column 3 metal oxide, a Column 4 metal oxide, a lanthanide oxide or composites thereof. When used to dimerize propylene, the catalyst can have at least 95% selectivity for 4-methyl-1-pentene. The catalyst can be macroporous, mesoporous, or microporous or a combination thereof. In some embodiments, the catalyst can have an average particle diameter of 100 to 600 microns, or at least, equal to, or between any two of 100 microns, 150 microns, 200 microns, 250 microns, 300 microns, 350 microns, 400 microns, 450 microns, 500 microns, 550 microns and 600 microns. The catalyst can have an average pore volume of 0.03 to 0.30 mL/g or at least, equal to, or between any two of 0.3 mL/g, 0.5 mL/g, 1 mL/g, 1.5 mL/g, 2 mL/g, 2.5 mL/g and 3 mL/g.

These and other non-limiting aspects of the present invention are discussed in further detail in the following sections.

C. Catalyst

1. Support Material

The support material can be a mixed metal oxide that includes a Column 1 metal oxide and/or a Column 3 metal oxide, a Column 4 metal oxide, and a lanthanide oxide, or mixtures, or composites thereof. Non-limiting examples of Column 1 metals includes Na, K, and Cs. Non-limiting examples of Columns 3, 4, and lanthanides include scandium (Sc), yttrium (Y), titanium (Ti), zirconium (Zr), lanthanum (La), cerium (Ce), promethium (Pm), or praseodymium (Pr). The support can also include hydrogen carbonates ($HCO_3$) and carbonates of metals. The amount of carbonates is 0.0 wt. % up to 49 wt. %, or less than, equal to or between 49 wt. %, 40 wt. %, 30 wt. %, 20 wt. %, 10 wt. %, 5 wt. %, 1 wt. % 0.5 wt. % 0.1 wt. % and 0.0 wt. % with the balance being oxide material (e.g., Column 1, 3, 4, or lanthanide oxides). In some cases, the prepared carrier can contain from 0.0 to 35 wt. % of the metal precursors (e.g., nitrates, carbonates, etc.) used to make the support. Non-limiting examples of the support material include potassium zirconate, potassium yttriate, and the like. The potassium zirconate can include one or more active phases. Non-limiting examples of active phases include $K_2Zr_8O_{17}$ (Powder Diffraction File (PDF) 00-014-0021), orthorhombic $K_2ZrO_3$ (PDF 00-018-1046), hexagonal or orthorhombic $K_2Zr_2O_5$ (PDF 00-020-0960), tetragonal $K_2Zr_3O_7$ (PDF 00-020-0960), hexagonal $K_4Zr_{11}O_{24}$ (PDF 00-030-1021), triclinic $K_4ZrO_4$ (PDF 00-031-1142), hexagonal $K_4Zr_5O_{12}$ (PDF 00-052-0353, PDF 01-071-1857), and the like. Without wishing to be bound by theory, it is believed that the main crystal structure is similar to $K_4Zr_5O_{12}$, which has a perovskite-similar crystal structure of potassium ions coordinated as cube octahedral and zirconium ions are inserted between the third and fourth layer as hexagonal rings. Other crystal structures of potassium zirconate can also be present (See, for example, the characterization of the support in the non-limiting Examples section).

Sodium yttriate can include one or more phases. Non-limiting examples of sodium yttriate phases include cubic $NaYO_2$ (PDF 00-032-1203), or the monoclinic $NaYO_2$ (PDF 01-070-1422), or a mixture of those two. In case of non-stoichiometric sodium yttriate, the overall solid is a composite made of sodium yttriate phase(s) and the excess element can be in the form of sodium oxide or yttrium oxide.

The support material can be prepared using known metal oxide support synthesis methodology or as illustrated in a non-limiting manner in the Examples. Non-limiting examples of preparation methods include co-precipitation, solid state chemistry sol-gel chemistry, molten salt chemistry, flame spray pyrolysis, hydrothermal spray and freeze drying, impregnation of precursor(s), or combinations thereof. In some embodiments, the method of preparation of the support can be co-precipitation of metal(s) precursor(s) (e.g., nitrate, chloride, acetate, carbonate, sulfate salts) in a protic solvent using a precipitating agent such as sodium hydroxide, lithium hydroxide, ammonium hydroxide, or carbonate or hydrogen carbonate. The resulting solid can then be filtered, dried and calcined at a given temperature. In another embodiment, the support material can be prepared using solid state chemistry methodology. This methodology can include grinding or milling at high energy solid powders of metal oxides, metal carbonates, and/or metal hydrogen carbonates together for a given time. The resulting solid can then be calcined to a given temperature. Another method of preparation can include sol-gel chemistry. Sol-gel chemistry can include dissolving the metal(s) precursor(s) (e.g., nitrate, chloride, acetate, carbonate, sulfate salts) in a protic solvent and reacting the salt in a first step with an organic compound (e.g., a carboxylic acid, or an amine) to form a organometallic complex. The organometallic complex can be heated to promote a polymerization-type coordination and evaporate the solvent. The resultant gel can then be dried and calcined to a given temperature. Molten salt methodology can also be used to prepare the support material. In this method a metal nitrate from Column 3 and/or Column 4 and/or the lanthanides can be mixed with a metal nitrite from Column 1 of the Periodic Table. The reaction between both solid can generate a reaction with a high exotherm, leading to a molten state that can create the desired mixed metal oxides. In some embodiments, the support material can include up to 60 wt. % of precursor(s) that are used to prepare the support material.

In the above methodology, calcining temperatures can range from 600° C. to 1200° C., 800° C. to 1100° C., or at least, equal to, or between any two of 600° C., 650° C., 700° C., 750° C., 800° C., 850° C., 900° C., 950° C., 1000° C., 1050° C., 1100° C., 1150° C. and 1200° C.

The support material can be shaped into various forms (e.g., tablets, lobes, spheres, etc.). By way of example, the support can be shaped into cylindrical tablets (opened or closed) by direct compression using known tableting methodology. The support material can be mixed with a binder (e.g., steric acid) and/or a lubricant (e.g., graphite). In other embodiments, the support material can be shaped in the form of trilobes or quadrilobe using extrusion molding techniques. By way of example, a carrier can be mixed with solvent (e.g., water or alcohol), binder (e.g., starch, cellulose, etc.), a surface tension modifier to form a paste that can flow freely through the die of the extruder.

2. Catalytic Metal

The catalyst can include a catalytic alkali metal or a composite thereof. Non-limiting examples of alkali metals include sodium (Na), potassium (K), Rubidium (Rb), and cesium (Cs). Non-limiting examples of alkali metal composites include NaK, NaCs, NaRb, KRb, KCs, and RbCs. In some embodiments, the catalytic alkali metal is K or a NaK composite. $Na_{23}K_{77}$-Eutectic can be obtained from commercial sources.

The catalyst of the present invention can include up to 10 wt. % of the metal, from 0.01 wt. % to 10 wt. %, or from 0.3 wt. % to 3 wt. % and all wt. % or at least, equal to, or between any two of 0.01 wt. %, 0.5 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. %, and 10 wt. %.

The catalytic metal can be combined with the support material using solution impregnation or molten state impregnation methodology or as illustrated in a non-limiting manner in the Examples. In solution impregnation, the alkaline metal precursor(s) (e.g., nitrate, carbonate, sulfate, chloride salts) can be impregnated in the support material using dry (without solvent) or wet (with solvent) techniques. The resulting solid can dried and calcined to a given temperature. In embodiments of the invention, the catalytic metal can be coated on the support material via chemical vapor deposition (MOCVD). Prior to reaction, the catalyst can be exposed under hydrogen in order to ensure that a catalytic metal is in the metal state as some oxidation occurs during calcination. In molten state impregnation, the alkali metal or mixtures thereof can be heated to a molten state at a temperature between 25° C. and 125° C., or 50° C. to 100° C., or at least, equal to, or between any two of 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., and 125° C. The molten metal can then be added to the shaped carrier in motion to provide a homogeneous dispersion of the molten metal on the support.

D. Method of Producing Branched Aliphatic Alkenes

Conditions sufficient for branched aliphatic alkene production (e.g., 4-methyl-1-pentene) include temperature, time, aliphatic alpha olefin concentration, space velocity, and pressure. The temperature range for branched aliphatic alkene production can range from about 120° C. to 200° C., or 140° C. to 170° C., or at least, equal to, or between 120° C., 130° C., 140° C., 150° C., 160° C., 170° C., 180° C., 190° C., and 200° C. A liquid hourly space velocity (LHSV) of reactant feed can be higher than 0.1 $h^{-1}$ or between 0.1 and 2 $h^{-1}$. The conversion of aliphatic alpha olefin can be carried out at a pressure of 5 MPa to 10 MPa, or at least, equal to, or between any two of 5 MPa, 6 MPa, 7 MPa, 8 MPa, 9 MPa, and 10 MPa. The conditions for branched aliphatic alkene production may be varied based on the type of the reactor.

The reaction of the methods and system disclosed herein can occur in a fixed bed process or reactor, plug-flow reactor, a circulating catalyst bed process or reactor or a batch reactor. The method and system can further include collecting or storing the produced branched aliphatic alkene product along with using the produced branched aliphatic alkene to produce a petrochemical or a polymer.

Referring to FIG. 1A, a system 100 is illustrated, which can be used to convert aliphatic alpha olefins to branched aliphatic alkenes with the mixed metal oxide supported catalytic alkali metal catalyst of the present invention. System 100 can include feed source 12 that includes the aliphatic alpha olefin and optional ethylene, first reactor 13, effluent separation column 14, and product purification fractionator 15. System 100 can further include one or more standby reactors 19 that are in regeneration mode or standby mode, in which the catalyst of standby reactors 19 has been regenerated while first reactor 13 is on-stream for converting aliphatic alpha olefins to branched aliphatic alkenes. The feed source 12 can be in fluid communication with first reactor 13 via an inlet (not shown) on the reactor. The aliphatic alpha olefin source can be configured such that it regulates the amount of aliphatic alpha olefin feed entering first reactor 13.

The aliphatic alpha olefins (e.g., olefins having a carbon number of 1 to 5, 2 to 4, or about 3) of the feed stream can be obtained from other process units and/or from commercial sources. The aliphatic alpha olefin feed stream can include at least 50 vol. %, or 82 vol. % to 95 vol. %, or 88 vol. % to 92 vol. % or 50 vol. %, 51 vol. %, 52 vol. %, 53 vol. %, 54 vol. %, 55 vol. %, 56 vol. %, 57 vol. %, 58 vol. %, 59 vol. %, 60 vol. %, 61 vol. %, 62 vol. %, 63 vol. %, 64 vol. %, 65 vol. %, 66 vol. %, 67 vol. %, 68 vol. %, 69 vol. %, 70 vol. %, 71 vol. %, 72 vol. %, 73 vol. %, 74 vol. %, 75 vol. %, 76 vol. %, 77 vol. %, 78 vol. %, 79 vol. %, 80 vol. %, 81 vol. %, 82 vol. %, 83 vol. %, 84 vol. %, 85 vol. %, 86 vol. %, 87 vol. %, 88 vol. %, 89 vol. %, 90 vol. %, 91 vol. %, 92 vol. %, 93 vol. %, 94 vol. %, 95 vol. %, or any value or range there between of an aliphatic alpha olefin with the balance being ethylene, saturated hydrocarbons, an inert gas or combinations thereof. Inert gases include nitrogen, helium or argon or combinations thereof. In some embodiments, the feed stream is a mixture of propylene, and ethylene and/or saturated hydrocarbons with the balance being an inert gas.

First reactor 13 and/or standby reactor(s) 19 can include a reaction zone 16 having the mixed metal oxide supported catalytic alkali metal catalyst 18 of the present invention. The amounts of aliphatic alpha olefin in feed source 12 and catalyst 18 used can be modified as desired to achieve a given amount of product produced by the system 100. Non-limiting examples of reactors that can be used include fixed-bed reactors, fluidized bed reactors, bubbling bed reactors, slurry reactors, rotating kiln reactors, plug-flow reactors or any combinations thereof when two or more reactors are used. Circulating catalyst bed reactors can allow the regeneration of used/deactivated catalysts in a continuous process. First reactor 13 can be flushed with an inert gas to remove trace amounts of water and air. Catalyst 18 can be activated by flowing a hydrogen source (e.g., a gaseous stream of hydrogen and argon) over the catalyst at a desired temperature (e.g., 150 to 350° C.). Contact of the aliphatic alpha olefin with catalyst can promote dimerization of the olefin(s) to produce an effluent stream 20. The effluent stream 20 can include dimerized product(s) such as a branched aliphatic alkene product produced in the reaction zone 16. Other products can include hexane, and branched $C_6$ hydrocarbons, branched or linear $C_9$ hydrocarbons, branched or linear $C_{12}$ hydrocarbons. By-products of the reaction can vary depending on the composition of the feed stream. Effluent stream 20 can further include unreacted aliphatic alpha olefins. Effluent stream 20 can exit reactor 13 and enter effluent separation column 14. Effluent separation column 14 can be configured to separate effluent stream 20 to form top stream 21 comprising unreacted aliphatic alpha olefins and bottom stream 22 comprising dimerized products (e.g., branched aliphatic alkenes) and isomers thereof. Top stream 21 can be split into recycle stream 23 comprising primarily unreacted aliphatic alpha olefins and purge stream 24. Recycle stream 23 can further be combined with feed source 12 to form combined feed stream 27, which is flowed into first reactor 13. Bottom stream 22 can be further fractionated in purification fractionator 15 to form product stream 25 comprising primarily the dimerized product including branched aliphatic alkenes (e.g., 4M1P) and isomer stream 26 comprising primarily one or more isomers of the dimerized product.

First reactor 13 and standby reactor(s) 19 can be pressurized reactors. First reactor 13 and standby reactor(s) can include one or more heating and/or cooling devices (e.g., insulation, electrical heaters, jacketed heat exchangers in the wall) or controllers (e.g., computers, flow valves, automated values, etc.) that are necessary to control the reactant flow, reaction temperature and/or pressure of the reaction mixture. The heating and/or cooling devices can use pressurized water and/or an organic compound as cooling media. While only one reactor is shown, it should be understood that multiple reactors can be housed in one unit or a plurality of reactors housed in one heat transfer unit.

Figure 1B:
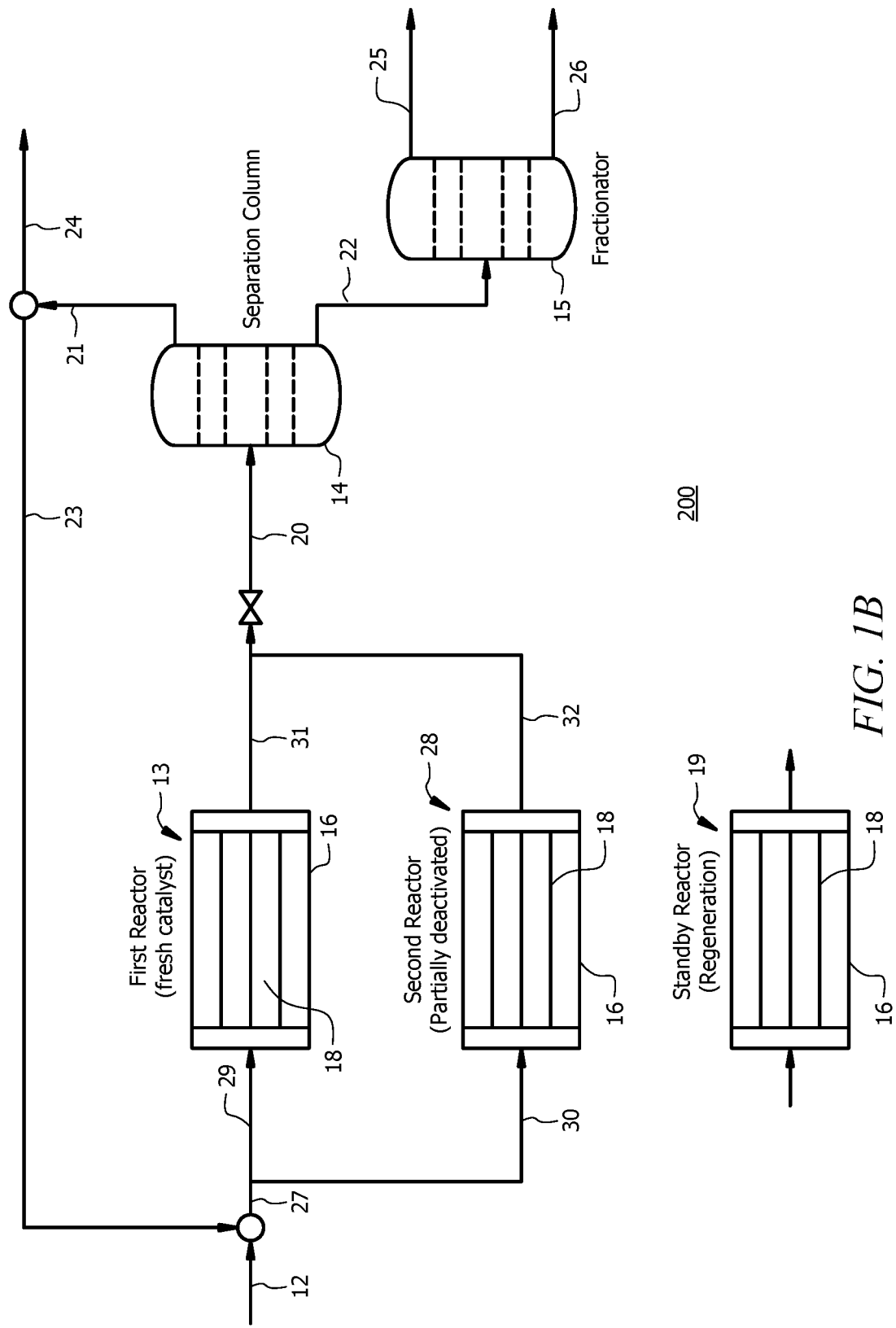

Referring to FIG. 1B, system 200 is illustrated, which can be used to convert aliphatic alpha olefins to branched aliphatic alkenes with the mixed metal oxide supported catalytic alkali metal catalyst of the present invention. In embodiments of the invention, system 200 includes all the units and streams of system 100 and further includes second reactor 28 operated in parallel configuration with first reactor 13. In system 200, combined feed stream 27 can be split into first feed stream 29 fed into an inlet of first reactor 13 and second feed stream 30 fed into an inlet of second reactor 28. Second reactor 28 can include the same or substantially the same catalyst as first reactor 13. In some aspects, catalyst in first reactor 13 and catalyst in second reactor 28 can have different levels of catalytic activity. For instance, first reactor 13 may include fresh catalyst and second reactor 28 may include partially deactivated catalyst. First effluent stream 31 from first reactor 13 and second effluent stream 32 from second reactor 28 can be combined to form effluent stream 20, which, as shown in FIG. 1B, is flowed into effluent separation column 14. In embodiments of the invention, system 200 can include more than 2 reactors (not shown), preferably 2 to 5 of the reactors, in parallel configuration. Catalyst activity levels of the more than 2 reactors can be different. Catalyst activity level for each of the reactors can be in a range of 30 to 100% of fresh catalyst and all ranges and values there between including ranges of 30 to 40%, 40 to 50%, 50 to 60%, 60 to 70%, 70 to 80%, 80 to 90%, and 90 to 100%. In embodiments of the invention, the two or more reactors can contain equal quantities or different quantities of the catalyst. Catalyst quantity ratio between the two or more reactors can be in a range of 10 to 100% and all ranges and values there between including ranges of 10 to 20%, 20 to 30%, 30 to 40%, 40 to 50%, 50 to 60%, 60 to 70%, 70 to 80%, 80 to 90%, and 90 to 100%. Compared to system 100 as shown in FIG. 1A, system 200 has the advantage since there is less variation in productivity hence less column operation variation.

Figure 1C:
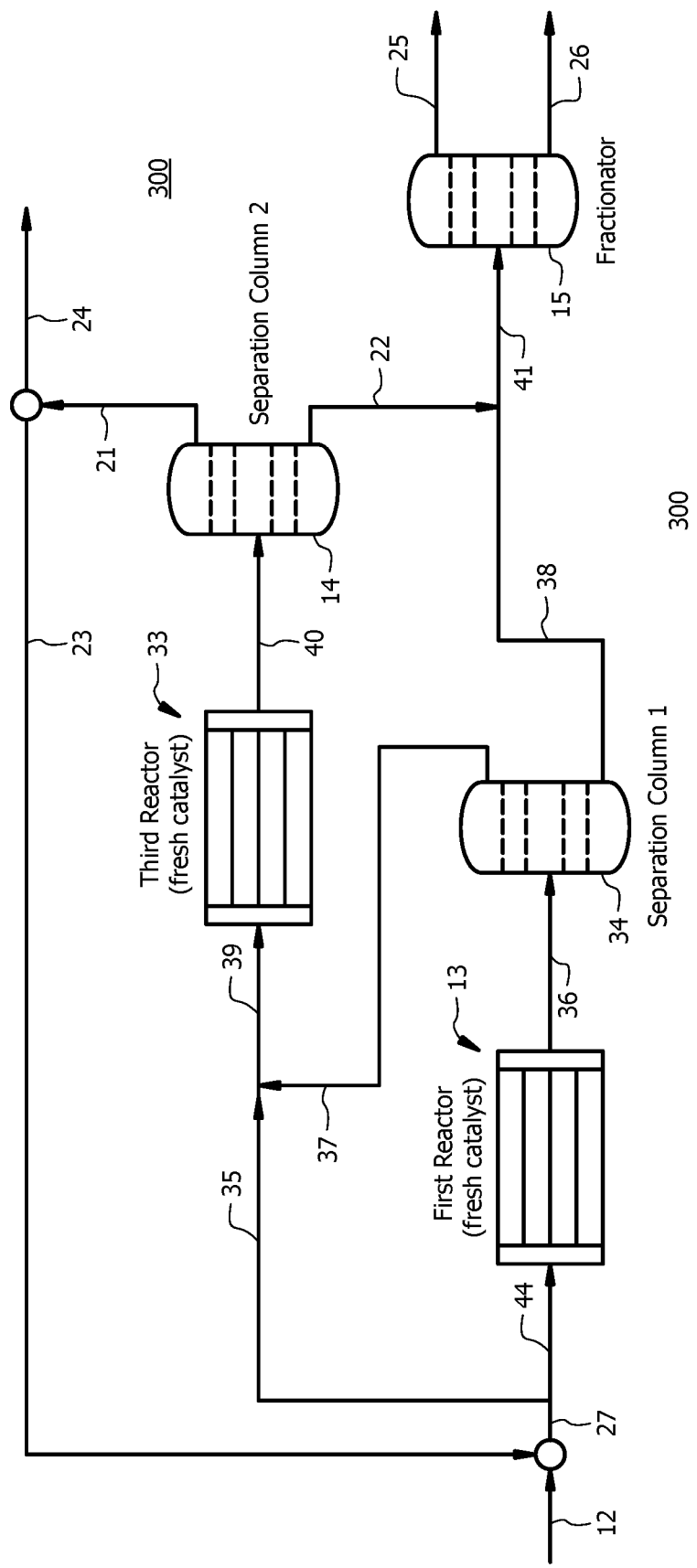

Referring to FIG. 1C, system 300 is illustrated, which can be used to convert aliphatic alpha olefins to branched aliphatic alkenes with the mixed metal oxide supported catalytic alkali metal catalyst of the present invention. System 300 can include all the units and streams of system 100 and can further include (i) third reactor 33 located downstream of first reactor 13 and (ii) intermediate separation column 34 located downstream of first reactor 13 and upstream of third reactor 33. According to embodiments of the invention, feed stream 27 can be split into first reactor feed stream 44 flowed into first reactor 13 and F-split stream 35. In embodiments of the invention, first reactor effluent stream 36 of first reactor 13 can be flowed into intermediate separation column 34, which is configured to separate first reactor effluent stream 36 to form (a) first top stream 37 comprising unreacted aliphatic alpha olefins and (b) first bottom stream 38 comprising dimerized product(s) and the isomers thereof. First top stream 37 can be combined with F-split stream 35 to form third reactor feed stream 39, which is flowed into third reactor 33. In embodiments of the invention, first reactor 13 and third reactor 33 include the same catalyst of the mixed metal oxide supported catalytic alkali metal of the present invention. First reactor 13 and third reactor 33 can be the same or substantially the same. Third reactor 33 can be configured to convert aliphatic alpha olefins of third reactor feed stream 39 to branched aliphatic alkenes. In embodiments of the invention, third reactor effluent stream 40 from third reactor 33 is separated in effluent separation column 14 to form top stream 21 comprising unreacted aliphatic alpha olefins and bottom stream 22 comprising dimerized products (e.g., branched aliphatic alkenes) and isomers thereof. Similar to system 100, in system 300, top stream 21 can be split into recycle stream 23 comprising primarily unreacted aliphatic alpha olefins and purge stream 24. Recycle stream 23 can further be combined with feed source 12 to form combined feed stream 27. Bottom stream 22 can be combined with first bottom stream 38 to form fractionator feed stream 41. Fractionator feed stream 41 can be separated in purification fractionator 15 to form product stream 25 comprising primarily the dimerized product including branched aliphatic alkenes (e.g., 4M1P) and isomer stream 26 comprising primarily one or more isomers of the dimerized product. According to embodiments of the invention, system 300 may not include F-split stream 35 such that feed stream 27 is directly flowed into first reactor 13 and first reactor 13 and third reactor 33 are in serial configuration. In embodiments of the invention, system 300 can include two or more reactors in series with a separation column disposed between two adjacent reactors. Each separation column between two closest reactors can be configured to remove dimerization product(s) and the isomers thereof from an effluent stream of a reactor located upstream of the separation column such that unreacted aliphatic alpha olefins fed into next reactor are not diluted. The separation column disposed between two closest reactors can prevent further isomerization of target dimerized product including branched aliphatic alkenes (e.g., 4M1P) by removing the dimerization product(s) and the isomers thereof from the feed stream of the reactor downstream of the separation column. System 300 comprising two or more of the reactors in series may be capable of increasing overall productivity of the targeted dimerized product(s) including branched aliphatic alkenes (e.g., 4M1P) compared to system 100 as shown in FIG. 1A.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Potassium Zirconate Support

Potassium zirconate material was synthesized using solid state methodology. The samples were prepared by using appropriate stoichiometric ratio to produce desired composition. A representative procedure to prepare 20 g of $K_5ZrO_{4.5}$ is provided. K and Zr precursors, $K_2CO_3$ (19.45 g) and $ZrO_2$ (6.87 g), were mixed and milled in a mortar and pestle. The mixed material was placed in a muffle furnace and heated to 1050° C. for 12 h with a ramp rate of 5° C./min. The resulting material after was cooled using the same ramp rate. The cooled material was milled and heated again for three iterations. Other compositions are made with the same methodology with varying the heating temperature and soaking time. The resulting powder mixture was characterized as having pure potassium zirconate or a multiphase system that consisted of single or multiple potassium zirconate phases with the existence of traces of other phases from the precursors.

Zirconium oxide ($ZrO_2$) starting precursor used in the process had a monoclinic crystal structure. The potassium carbonate ($K_4C_2O_6$) phase precursor can be used with either the hexagonal structure or monoclinic structure. The hexagonal structure was used, each of which with its corresponding space group. About 5 wt. % of the precursors existed after the calcination.

Figure 2:
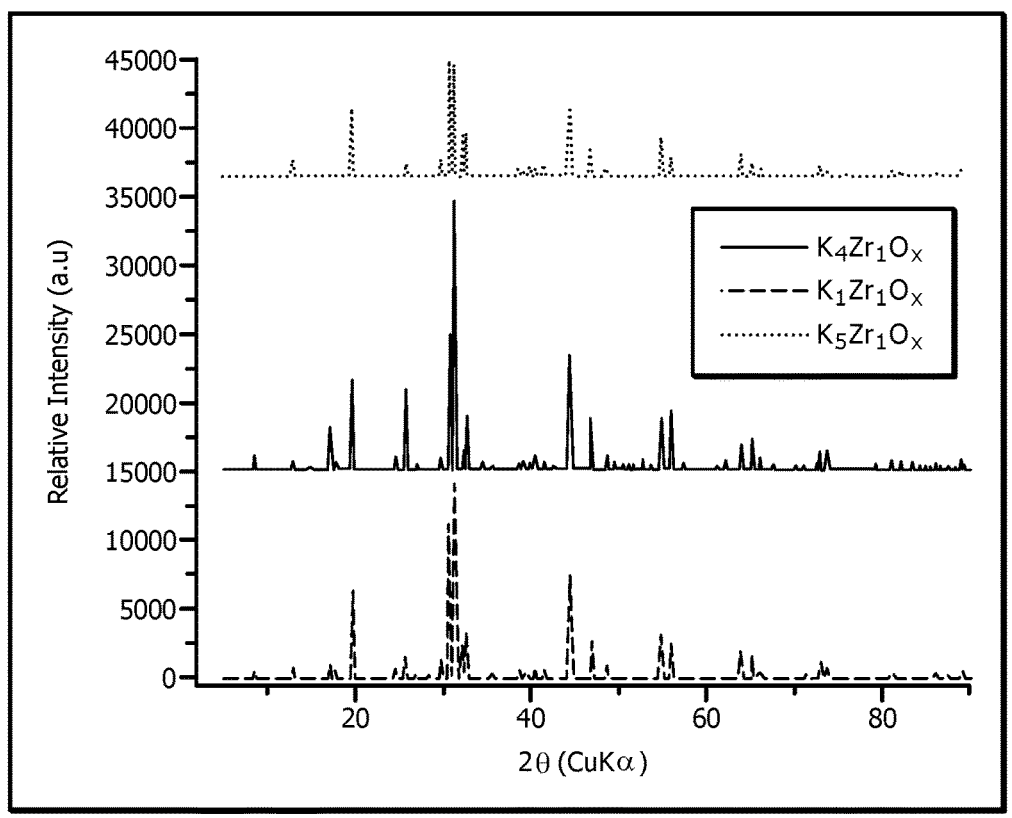
FIG. 2 is an X-ray diffraction (XRD) of the potassium zirconate support material of the present invention.

The potassium zirconate phases were characterized by X-ray diffraction (XRD) using a PANalytical Empyrean diffractometer (Malvern Panalytical, United Kingdom). The specimen was scanned at room temperature 25° C. on a regular sample holder used in the range of °5<° 2θ<°100 with step size of ° 0.0130 and fixed divergence slit with ° 0.2177 slit size. The anode material used is copper and the general generator settings are 40 mA, 45 kV. FIG. 2 depicts XRD patterns of the potassium zirconate carriers made using the procedure of Example 1. The following phases were detected triclinic $K_4ZrO_4$ (PDF 00-031-1142) and hexagonal for KZrO and $K_5ZrO_x$.

The main predicted potassium zirconate phase was believed to have a similar crystal structure of $K_4Zr_5O_{12}$ which—according the literature—has a perovskite-similar crystal structure of potassium ions coordinated as cube octahedral and zirconium ions are inserted between the third and fourth layer as hexagonal rings.

Example 2

Synthesis of Sodium Yttriate Support Material

Sodium yttriate material was synthesized using a co-precipitation method. Yttrium nitrate ($Y(NO_3)_3 \cdot 6H_2O$, 13.31 g) starting precursor was dissolved in a minimal amount of water (20 mL). The corresponding amount of sodium carbonate ($Na_2CO_3$, 3.72 g) was added to the solution. The solution was heated to 70° C. As the water evaporated, co-precipitation occurred. The solid was recovered, dried and then calcined at 1050° C. until the crystal structure of sodium yttriate was formed. The powder can be sieved to obtain a powder having a particle size of 100 to 300 microns.

Figure 3:
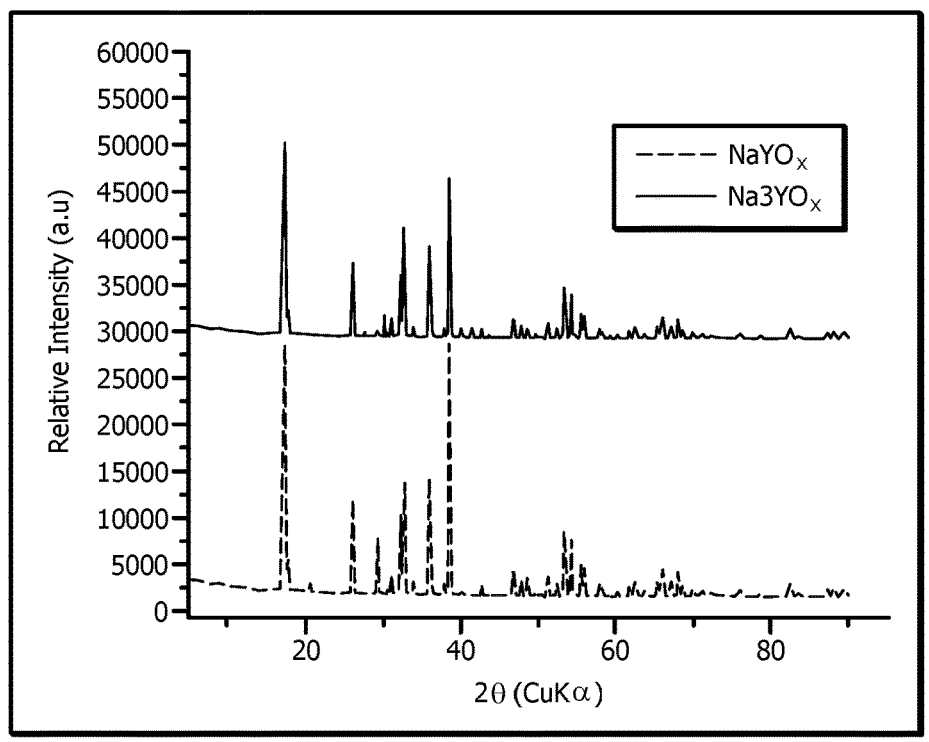
FIG. 3 is an XRD of the sodium yttriate support material of the present invention.

The resulting powder mixture was characterized by XRD to have pure sodium yttriate or a multiphase system that consists of single sodium yttriate phase with the existence of other phases from the precursors. The produced sodium yttriate included a cubic $NaYO_2$ (PDF 00-032-1203) phase. In case of non-stoichiometric sodium yttriate, the overall solid is a composite made of sodium yttriate phase(s) and the excess element considered to be sodium oxide or yttrium oxide. FIG. 3 shows the XRD patterns for $NaYO_x$ and $Na_3YO_x$.

Example 3

Synthesis of Metallic Sodium on Sodium Yttriate Support Material

Sodium yttriate support (10 g) material of Example 2 having a particle size of 100 to 300 microns was placed in a container. The container was flushed with inert gas to remove traces of water and air. The sealed container was heated to 300° C. under agitation for 2 h. The temperature was then set to 200° C. and potassium metal (5 wt. % by total weight of catalyst) was introduced to the container. The resulting mixture was agitated for 1 h to homogeneously distribute the molten metal on the support material.

Example 4

Synthesis of Metallic Sodium or NaK on Potassium Zirconate Support Material

The potassium zirconate (49 g, Example 1) was mixed with graphite (2 wt. % based on the total weight of the catalyst) in a blender to ensure homogeneous distribution of the additive prior to be tableted to 3×3 millimeter tablets. The obtained tablets exhibited a radial and axial mechanical strength of 200 to 400 daN and a density of 1 grams per centimeter cube to 4 grams per centimeter cube as function of particle size used. The as-prepared tablets (approximately 10 g by weight) were loaded into a container and flushed by inert gas to remove water and oxygen. The container was agitated and heated to 300° C. for 2 hours. As produced fine particles during the first step of the process were removed from the container. The container was again agitated at 200° C. and potassium metal or potassium and sodium metal was introduced (5 wt. % based on the total weight of the catalyst). The resulting mixture was kept under agitation for 1 h to ensure homogeneous distribution of the melted metal on the potassium zirconate tablet.

Example 5

Synthesis of Branched Aliphatic Alkenes from Propylene—Batch Reactor

In an autoclave catalyst (2 g) from Example 3 or comparative sample of $K_2CO_3$ and a stirring bar were placed. The reactor was closed and the weight recorded. The reactor was cooled to 0° C., placed on a balance and propylene was condensed into the reactor until a weight increase of 8.5 times the original weight (17 g) was achieved. Subsequently, the reactor was carefully vented until the increase in weight was exactly 8.5 times the original weight (17 g). The reactor was then placed in an oil bath and maintained at 150° C. while stirring. A gas manifold was connected to the autoclave head valve to allow sampling by two successive decompression stages. Samples (0.2 mL of product) were withdrawn with the at regular time intervals and were analyzed by GC. After 24 hours, the final weight of the reactor was recorded, the reactor was cooled down to 0° C. and carefully depressurized. Final weight was recorded to determine the yield. The liquid product and spent catalyst were separated by filtration, (diluted with heptane where needed). The liquid was analyzed by GC-MS (Agilent 5977A-MSD/mounted with a DB1 column and FID detector (Agilent Technologies, USA)) and the solid was analyzed by XRD. The results are listed in Table 1. Selectivity for 4-methyl-1-pentene (4M1P) was calculated using the following equation:

$$\text{Selectivity } 4M1P = \frac{\text{Moles of } 4M1P \text{ produced}}{2 \times \text{Moles of Propylene converted}}$$

TABLE 1

|  | $K_2CO_3$ | $NaYO_2$ | $Na_3YO_x$ |
|---|---|---|---|
| Metal loading | 3% Na | 3% Na | 3% Na |
| Temperature | 150 | 150 | 150 |

TABLE 1-continued

|  | $K_2CO_3$ | $NaYO_2$ | $Na_3YO_x$ |
|---|---|---|---|
| Initial pressure | 75 | 76 | 77 |
| Conversion after 24 h | 17 | 12 | 15 |
| 4M1P Selectivity observed after 6 h | 85 | 55 | 78 |
| 4M1P Selectivity observed after 12 h | 82 | 65 | 80 |
| 4M1P Selectivity observed after 18 h | 78 | 75 | 82 |
| 4M1P Selectivity observed after 24 h | 75 | 80 | 82 |

Example 6

Synthesis of Branched Aliphatic Alkenes from Propylene—Plug Flow Reactor

Approximately 4 g of the shaped catalyst of Example 4 catalyst or comparative catalyst $K_2CO_3$ was loaded into a reactor under inert atmosphere. The reactor was then connected to a gas feed section and located into a furnace to ensure temperature control. The overall system was flushed with inert gas to ensure removal of traces of water and air. Propylene at 75 bar (7.5 MPa) was then used to carry the reaction at a temperature between 145 and 165° C. and a LHSV between 0.2 and 1 $h^{-1}$. The pressure was controlled by a backpressure regulator system and outlet gas composition was continuously analyzed by gas chromatography. The results are listed in Table 2. $C_6$ refers to total amount of linear and branched $C_6$ hydrocarbons. Conversion was determined using the following equation:

$$\text{Conversion} = \frac{\text{(Moles of Propylene in} - \text{Moles of propylene out)}}{\text{Moles of Propylene in}}$$

TABLE 2

|  | $K_2CO_3$ | $K_5ZrOx$ | $K_5ZrOx$ | $K_5ZrOx$ |
|---|---|---|---|---|
| Active Phase | K | K | K | Na/K |
| Active phase | 5 | 5 | 7 | 7 |
| content (% w/w) | | | | |
| T | 150 | 150 | 150 | 150 |
| p | 75 | 75 | 75 | 75 |
| Res. t. | 7.47 | 7.46 | 7.54 | 7.50 |
| Conv | 30 | 8 | 40 | 35 |
| 4M1P/MP | 95.4 | 96.2 | 93.2 | 96.1 |
| MP/$C_6$ | 92.4 | 95 | 93.8 | 93.7 |

From the data, it was determined that a catalytic active alkali metal on a mixed oxide support that includes an alkali metal and at least one of a Column 3, Column 4, or lanthanide metal can effectively catalyze the conversion of aliphatic alpha olefins (e.g., propylene) to a branched aliphatic alkene (e.g., 4-methyl-1-pentene). Specifically, 7 wt. % of a K or NaK composite on a $K_5ZrO_x$ where x balances the valance of the mixed metal oxide produces 4-methyl-1-pentene at a similar conversion and similar to higher selectivity than potassium carbonate, thus providing a technical solution to problems associated (e.g., structural collapse of the catalyst) associated with carbonate catalysts.

Example 7

Synthesis of Branched Aliphatic Alkenes in a Single Reactor System

Simulations were conducted in ASPEN™ Plus (Version 10) for a reaction system as shown in FIG. 1A. The reaction kinetics in the reactor was obtained from experiments conducted in a lab-scale single-reactor 4M1P production system. The simulations were set up to produce 99.0 mol. % 4M1P in the product stream (labeled as product stream 25 in FIG. 1A), which was achieved by adjusting the parameters of the separation equipment (e.g., effluent separation column 14 and product purification fractionator 15 in FIG. 1A). The compositions, flow rates, and conditions (temperature and pressure) for each stream of the reaction system as shown in FIG. 1A are shown in Table 3. The overall conversion rate of $C_3H_6$ was 50.8%. The selectivity of 4M1P was 89.9%. The product flowrate of the system was 6.42 ton/hr.

TABLE 3

| Stream | Feed source stream | Recycle stream | Combined feed stream | First effluent stream | Top stream | Purge stream | Bottom stream | Isomer stream | Product stream |
|---|---|---|---|---|---|---|---|---|---|
| Fraction (mol. %) | | | | | | | | | |
| $C_3H_6$ | 0.995 | 0.825 | 0.906 | 0.578 | 0.825 | 0.825 | 0.002 | 0.000 | 0.003 |
| $C_3H_8$ | 0.005 | 0.175 | 0.094 | 0.123 | 0.175 | 0.175 | 0.001 | 0.000 | 0.002 |
| 4M1P | 0.000 | $1.02 \times 10^{-5}$ | $5.38 \times 10^{-6}$ | 0.269 | $1.02 \times 10^{-5}$ | $1.02 \times 10^{-5}$ | 0.896 | 0.226 | 0.990 |
| 4M2P-cis | 0.000 | $1.10 \times 10^{-7}$ | $5.82 \times 10^{-8}$ | 0.011 | $1.10 \times 10^{-7}$ | $1.10 \times 10^{-7}$ | 0.012 | 0.058 | 0.005 |
| 4M2P-trans | 0.000 | $1.88 \times 10^{-7}$ | $9.92 \times 10^{-8}$ | $1.29 \times 10^{-7}$ | $1.88 \times 10^{-7}$ | $1.88 \times 10^{-7}$ | 0.024 | 0.190 | $4.09 \times 10^{-4}$ |
| 1-Hex | 0.000 | $3.62 \times 10^{-7}$ | $1.91 \times 10^{-7}$ | 0.020 | $3.62 \times 10^{-7}$ | $3.62 \times 10^{-7}$ | 0.065 | 0.526 | $1.53 \times 10^{-6}$ |
| Total Flow (kmol/h) | 178.19 | 199.44 | 377.63 | 290.73 | 203.51 | 4.07 | 87.22 | 10.80 | 76.42 |
| Total Flow (kg/h) | 7500.00 | 8463.10 | 15963.09 | 15963.1 | 8635.81 | 172.72 | 7327.3 | 908.6 | 6418.70 |
| Temp. (° C.) | 150.00 | 150.00 | 149.99 | 150.00 | 42.93 | 42.93 | 181.82 | 136.3 | 117.47 |
| Pressure (bar) | 75.00 | 75.00 | 75.00 | 75.00 | 17.24 | 17.24 | 17.60 | 7.00 | 5.50 |

Example 8

Synthesis of Branched Aliphatic Alkenes in a System Including Two Parallel Reactors Simulations were conducted in ASPEN™ Plus (Version 10) for a reaction system as shown in FIG. 1B. The reaction kinetics in the reactors of the reaction system was obtained from experiments conducted in a lab-scale single-reactor 4M1P production system. The simulations were set up to produce 99.0 mol. % 4M1P in the product stream (labeled as product stream 25 in FIG. 1B), which was achieved by adjusting the parameters of the separation equipment (e.g., effluent separation column 14 and product purification fractionator 15 in FIG. 1B). The compositions, flow rates, and conditions (temperature and pressure) for each stream of the reaction system as shown in FIG. 1B are shown in Table 4. The conversion rates in the first reactor (labeled as first reactor 13 in FIG. 1B) and the second reactor (labeled as second reactor 28 in FIG. 1B) were 46.6% and 40.3%, respectively. The overall conversion rate of $C_3H_6$ was 43.4%. The selectivity of 4M1P in the first reactor and the second reactor were 90.1% and 90.5%, respectively. The overall selectivity of 4M1P was 90.3%. The product flowrate of the system was 6.38 ton/hr.

adjusting the parameters of the separation equipment (e.g., effluent separation column 14 and product purification fractionator 15 in FIG. 1C). The compositions, flow rates, and conditions (temperature and pressure) for each stream of the reaction system as shown in FIG. 1C are shown in Table 5. The conversion rates in the first reactor (labeled as first reactor 13 in FIG. 1C) and the third reactor (labeled as third reactor 33 in FIG. 1C) were 48.9% and 47.3%, respectively. The overall conversion rate of $C_3H_6$ was 64.3%. The selectivity of 4M1P in the first reactor and the third reactor were 90.1% and 90.4%, respectively. The overall selectivity of 4M1P was 90.2%. The product flowrate of the system was 6.38 ton/hr.

The systems and process described herein can also include various equipment that is not shown and is known to one of skill in the art of chemical processing. For example, some controllers, piping, computers, valves, pumps, heaters,

TABLE 4

| Stream | Feed source stream | Recycle stream | Combined feed stream | Second feed stream | First effluent stream | Second effluent stream |
|---|---|---|---|---|---|---|
| Mole Frac. (%) | | | | | | |
| $C_3H_6$ | 0.995 | 0.864 | 0.918 | 0.918 | 0.624 | 0.673 |
| $C_3H_8$ | 0.005 | 0.136 | 0.082 | 0.082 | 0.104 | 0.100 |
| 4M1P | 0.000 | $6.44 \times 10^{-6}$ | $3.79 \times 10^{-6}$ | $3.79 \times 10^{-6}$ | 0.245 | 0.205 |
| 4M2P-Cis | 0.000 | $6.86 \times 10^{-8}$ | $4.04 \times 10^{-8}$ | $4.04 \times 10^{-8}$ | 0.010 | 0.008 |
| 4M2P-Trans | 0.000 | $1.19 \times 10^{-7}$ | $7.01 \times 10^{-8}$ | $7.01 \times 10^{-8}$ | $8.92 \times 10^{-8}$ | $8.60 \times 10^{-8}$ |
| 1-Hex | 0.000 | $2.37 \times 10^{-7}$ | $1.40 \times 10^{-7}$ | $1.40 \times 10^{-7}$ | 0.017 | 0.014 |
| Total flow (kmol/h) | 178.2 | 254.83 | 216.51 | 216.51 | 170.21 | 176.49 |
| Total Flow (kg/h) | 7500.00 | 10793 | 9146.52 | 9146.5 | 9146.5 | 9146.5 |
| Temp. (° C.) | 150.00 | 150.00 | 149.99 | 149.99 | 150.00 | 150.00 |
| Pressure (bar) | 75.00 | 75.00 | 75.00 | 75.00 | 75.00 | 75.00 |

| Stream | Effluent stream | Top stream | Purge stream | Bottom stream | Isomer stream | Product stream |
|---|---|---|---|---|---|---|
| Mole Frac. (%) | | | | | | |
| $C_3H_6$ | 0.649 | 0.864 | 0.864 | 0.003 | 0.000 | 0.003 |
| $C_3H_8$ | 0.102 | 0.136 | 0.136 | 0.001 | 0.000 | 0.002 |
| 4M1P | 0.225 | $6.44 \times 10^{-6}$ | $6.44 \times 10^{-6}$ | 0.899 | 0.253 | 0.990 |
| 4M2P-Cis | 0.003 | $6.86 \times 10^{-8}$ | $6.86 \times 10^{-8}$ | 0.011 | 0.058 | 0.005 |
| 4M2P-Trans | 0.006 | $1.19 \times 10^{-7}$ | $1.19 \times 10^{-7}$ | 0.023 | 0.183 | $3.61 \times 10^{-4}$ |
| 1-Hex | 0.016 | $2.37 \times 10^{-7}$ | $2.37 \times 10^{-7}$ | 0.063 | 0.505 | $1.43 \times 10^{-6}$ |
| Total flow (kmol/h) | 346.70 | 260.03 | 5.20 | 86.68 | 10.73 | 75.95 |
| Total Flow (kg/h) | 18292 | 11013 | 220.27 | 7279.6 | 902.67 | 6376.94 |
| Temp. (° C.) | 98.97 | 42.69 | 42.69 | 181.67 | 136.08 | 117.26 |
| Pressure (bar) | 20.00 | 17.24 | 17.24 | 17.60 | 7.00 | 5.50 |

Example 9

Synthesis of Branched Aliphatic Alkenes in a System Including Two Serial Reactors Simulations were conducted in ASPEN™ Plus (Version 10) for a reaction system as shown in FIG. 1C. The reaction kinetics in the reactors of the reaction system was obtained from experiments conducted in a lab-scale single-reactor 4M1P production system. The simulations were set up to produce 99.0 mol. % 4M1P in the product stream (labeled as product stream 25 in FIG. 1C), which was achieved by thermocouples, pressure indicators, mixers, heat exchangers, and the like may not be shown.

In the context of the present invention, at least the following 23 embodiments are shown. Embodiment 1 is a method of producing a branched aliphatic alkene. The method includes reacting a feed stream containing aliphatic alpha olefins(s) with a supported alkali metal or alkali metal composite catalyst to produce the branched aliphatic alkene, wherein the support contains a mixed metal oxide including a Column 1 metal and at least one of a Column 3 metal, a Column 4 metal, or a lanthanide, wherein the catalyst has less than 50 wt. % of a metal carbonate. Embodiment 2 is the method of embodiment 1, wherein the alkali metal is sodium (Na), potassium (K), cesium (Cs), or a composite, or a mixture thereof. Embodiment 3 is the method of embodiment 2, wherein the alkali metal is K or the alkali metal composite is NaK. Embodiment 4 is the method of any one of embodiments 1 to 3, wherein the Column 3 metal oxide contains scandium (Sc) or yttrium (Y), preferably Y. Embodiment 5 is the method of any one of embodiments 1 to 4, wherein the Column 4 metal oxide contains titanium (Ti), zirconium (Zr), hafnium (Hf), or combinations thereof, preferably Zr. Embodiment 6 is the method of any one of embodiments 1 to 5, wherein the lanthanide oxide contains lanthanum (La), cerium (Ce), promethium (Pm), or praseodymium (Pr), preferably La. Embodiment 7 is the method of any one of embodiments 1 to 6, wherein the Column 1 metal oxide contains Na, K, or Cs, more preferably K. Embodiment 8 is the method of any one of embodiments 1 to 7, wherein catalyst includes 0.1 to 10 wt. % of the alkali metal, preferably 1 to 9 wt. %, more preferably 3 to 8 wt. %. Embodiment 9 is the method of any one of embodiments 2 to 8, wherein the catalyst is K metal supported on sodium yttriate, potassium zirconate, or a mixture thereof. Embodiment 10 is the method of any one of embodiments 2 to 8, wherein the catalyst is NaK metal composite supported on sodium yttriate, potassium zirconate, or a mixture thereof. Embodiment 11 is the method of any one of embodiments 1 to 10, wherein the support is macroporous, mesoporous, or microporous or a combination thereof. Embodiment 12 is the method of any one of embodiments 1 to 11, wherein the catalyst has an average particle diameter of 100 to 600 microns, an average pore volume of 0.03 to 0.30 mL/g, or both. Embodiment 13 is the method of any one of embodiments 1 to 12, wherein the aliphatic alpha olefins have a carbon number of 1 to 5, preferably 2 to 4, more preferably 3. Embodiment 14 is the method of any one of embodiments 1 to 13, wherein the feed stream contains propylene. Embodiment 15 is the method of embodiment 14, wherein the feed stream further contains ethylene, a saturated hydrocarbon, or both. Embodiment 16 is the method of any one of embodiments 1 to 15, wherein the branched aliphatic alkene has a carbon number from 4 to 10, preferably 4 to 8, more preferably 6, more preferably 4-methyl-1-propene. Embodiment 17 is the method of any one of embodiments 1 to 16, wherein reaction pressure is between 5 MPa and 10 MPa, the reaction temperature is 120 to 200° C. more preferably 140 to 170° C., or both, or liquid hourly space velocity of 0.1 and 2 h$^{-1}$. Embodiment 18 is the method of embodiment 17, wherein the reaction is conducted in a reaction system including a pressurized reactor. Embodiment 19 is the method of embodiment 18, wherein the reaction system includes 2 to 5 reactors in parallel, wherein at least 2 of the 2 to 5 reactors have the catalyst with different catalytic activity levels, and at least one of the 2 to 5 reactors is in regeneration mode. Embodiment 20 is the method of embodiment 18, wherein the reaction system includes a first reactor and a second reactor in series, and a separation column downstream of the first reactor and upstream of the second reactor, wherein said separation column is configured to remove the branched aliphatic alkene and isomers thereof from an effluent of the first reactor to produce an inlet stream for the second reactor. Embodiment 21 is the method of any of embodiments 17 to 20, wherein the catalyst is potassium metal or a NaK composite on sodium zirconate and the branched aliphatic alkene selectivity is at least 60% after 6 hours. Embodiment 22 is the method of embodiment 21, wherein the catalyst is a NaK composite on a potassium zirconate and the 4-methyl-1-pentene to methyl pentene ratio is at least 93%.

Embodiment 23 is a catalyst for producing a branched aliphatic alkene. The catalyst contains potassium (K) metal or a NaK metal composite on a metal oxide support including a mixed metal oxide of a Column 1 metal and at least one of a Column 3 metal, a Column 4 metal, a lanthanide, wherein the catalyst has less than 50 wt. % of a metal carbonate.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

TABLE 5

| Stream | Feed source stream | Recycle stream | F-Split stream | First feed stream | First reactor effluent stream | First top stream | First bottom stream | Third reactor feed stream |
|---|---|---|---|---|---|---|---|---|
| Fraction (mol. %) | | | | | | | | |
| $C_3H_6$ | 0.995 | 0.743 | 0.890 | 0.890 | 0.581 | 0.805 | 0.003 | 0.845 |
| $C_3H_8$ | 0.005 | 0.257 | 0.110 | 0.110 | 0.141 | 0.195 | 0.003 | 0.155 |
| 4M1P | 0.000 | $7.43 \times 10^{-6}$ | $3.11 \times 10^{-6}$ | $3.11 \times 10^{-6}$ | 0.251 | $7.32 \times 10^{-6}$ | 0.895 | $5.31 \times 10^{-6}$ |
| 4M2P-Cis | 0.000 | $7.68 \times 10^{-8}$ | $3.22 \times 10^{-8}$ | $3.22 \times 10^{-8}$ | 0.003 | $7.94 \times 10^{-8}$ | 0.012 | $5.68 \times 10^{-8}$ |
| 4M2P-Trans | 0.000 | $1.33 \times 10^{-7}$ | $5.55 \times 10^{-8}$ | $5.55 \times 10^{-8}$ | 0.007 | $1.38 \times 10^{-7}$ | 0.023 | $9.84 \times 10^{-8}$ |
| 1-Hex | 0.000 | $2.61 \times 10^{-7}$ | $1.09 \times 10^{-7}$ | $1.09 \times 10^{-7}$ | 0.018 | $2.73 \times 10^{-7}$ | 0.064 | $1.95 \times 10^{-7}$ |
| Flow (kmol/h) | 178.19 | 128.31 | 104.21 | 202.29 | 158.25 | 113.94 | 44.31 | 218.15 |
| Flow (kg/h) | 7500.00 | 5465.88 | 4408.40 | 8557.48 | 8557.48 | 4839.43 | 3718.05 | 9247.83 |

TABLE 5-continued

| | | | | | | | | |
|---|---|---|---|---|---|---|---|---|
| Temp. (° C.) | 150.00 | 150.00 | 149.97 | 149.97 | 150.00 | 43.05 | 181.28 | 104.62 |
| Pres. (bar) | 75.00 | 75.00 | 75.00 | 75.00 | 75.00 | 17.24 | 17.60 | 75.00 |

| Stream | Third reactor effluent stream | Top stream | Bottom stream | Purg stream | Fractionator-feed stream | Isomer stream | Product stream |
|---|---|---|---|---|---|---|---|
| Fraction (mol. %) | | | | | | | |
| $C_3H_6$ | 0.557 | 0.743 | 0.001 | 0.743 | 0.002 | $8.00 \times 10^{-51}$ | 0.002 |
| $C_3H_8$ | 0.193 | 0.257 | 0.001 | 0.257 | 0.002 | $1.74 \times 10^{-48}$ | 0.002 |
| 4M1P | 0.226 | $7.43 \times 10^{-6}$ | 0.903 | $7.43 \times 10^{-6}$ | 0.899 | 0.220 | 0.990 |
| 4M2P-Cis | 0.003 | $7.68 \times 10^{-8}$ | 0.011 | $7.68 \times 10^{-8}$ | 0.011 | 0.057 | 0.005 |
| 4M2P-Trans | 0.006 | $1.33 \times 10^{-7}$ | 0.023 | $1.33 \times 10^{-7}$ | 0.023 | 0.192 | $4.10 \times 10^{-4}$ |
| 1-Hex | 0.015 | $2.61 \times 10^{-7}$ | 0.062 | $2.61 \times 10^{-7}$ | 0.063 | 0.531 | $1.47 \times 10^{-6}$ |
| Flow (kmol/h) | 174.57 | 130.93 | 43.64 | 2.62 | 87.95 | 10.36 | 77.59 |
| Flow (kg/h) | 9247.83 | 5577.42 | 3670.41 | 111.55 | 7388.45 | 871.84 | 6516.61 |
| Temp. (° C.) | 150.00 | 43.45 | 182.29 | 43.45 | 181.78 | 136.37 | 117.46 |
| Pres. (bar) | 75.00 | 17.24 | 17.60 | 17.24 | 17.60 | 7.00 | 5.50 |

The invention claimed is:

1. A method of producing a branched aliphatic alkene, the method comprising reacting a feed stream comprising aliphatic alpha olefins(s) with a supported alkali metal or alkali metal composite catalyst to produce the branched aliphatic alkene, wherein the support comprises a mixed metal oxide comprising a Column 1 metal and at least one of a Column 3 metal, a Column 4 metal, or a lanthanide, wherein the catalyst has less than 50 wt. % of a metal carbonate,
wherein the reaction is conducted in a reaction system comprising a pressurized reactor;
wherein the reaction system comprises 2 to 5 reactors in parallel, or
wherein the reaction system comprises a first reactor and a second reactor in series, and a separation column downstream of the first reactor and upstream of the second reactor.

2. The method of claim 1, wherein the alkali metal is sodium (Na), potassium (K), cesium (Cs), or a composite, or a mixture thereof.

3. The method of claim 2, wherein the alkali metal is K or the alkali metal composite is NaK.

4. The method of claim 2, wherein the catalyst is K metal supported on sodium yttriate, potassium zirconate, or a mixture thereof.

5. The method of claim 2, wherein the catalyst is NaK metal composite supported on sodium yttriate, potassium zirconate, or a mixture thereof.

6. The method of claim 1, wherein the support comprises Column 3 metal oxide comprises scandium (Sc) or yttrium (Y).

7. The method of claim 1, wherein the Column 4 metal oxide comprises titanium (Ti), zirconium (Zr), hafnium (Hf), or combinations thereof.

8. The method of claim 1, wherein the lanthanide oxide comprises lanthanum (La), cerium (Ce), promethium (Pm), or praseodymium (Pr).

9. The method of claim 1, wherein the Column 1 metal oxide comprises Na, K, or Cs.

10. The method of claim 1, wherein catalyst comprises 0.1 to 5 wt. % of the alkali metal.

11. The method of claim 1, wherein the support is macroporous, mesoporous, or microporous or a combination thereof.

12. The method of claim 1, wherein the catalyst has an average particle diameter of 100 to 600 microns, an average pore volume of 0.03 to 0.30 mL/g, or both.

13. The method of claim 1, wherein the aliphatic alpha olefins have a carbon number of 2 to 7.

14. The method of claim 1, wherein the feed stream comprises propylene.

15. The method of claim 14, wherein the feed stream further comprises ethylene, a saturated hydrocarbon, or both.

16. The method of claim 1, wherein the branched aliphatic alkene has a carbon number from 4 to 10.

17. The method of claim 1, wherein the amount of metal carbonate is equal to or between 49 wt. % and 0.1 wt. %.

18. The method of claim 1, wherein the reaction is conducted in a reaction system comprising a pressurized reactor.

19. The method of claim 18, wherein at least 2 of the 2 to 7 reactors in parallel have the catalyst with different catalytic activity levels, and at least one of the 2 to 5 reactors is in regeneration mode.

* * * * *

UNITED STATES PATENT AND TRADEMARK OFFICE
CERTIFICATE OF CORRECTION

PATENT NO. : 11,498,888 B2  
APPLICATION NO. : 17/250360  
DATED : November 15, 2022  
INVENTOR(S) : Gregory Biausque et al.

Page 1 of 1

It is certified that error appears in the above-identified patent and that said Letters Patent is hereby corrected as shown below:

In the Claims

In Claim 10, Column 20, Line 34, please delete "5 wt.%" and insert --10 wt.%-- therefor.

In Claim 13, Column 20, Line 43, please delete "7" and insert --5-- therefor.

In Claim 19, Column 20, Line 57, please delete "7" and insert --5-- therefor.

Signed and Sealed this  
Seventh Day of January, 2025

Derrick Brent  
*Acting Director of the United States Patent and Trademark Office*